(12) United States Patent
Evans

(10) Patent No.: US 10,952,758 B1
(45) Date of Patent: Mar. 23, 2021

(54) KIDNEY STONE TURBULENT FLOW IRRIGATOR AND SYSTEM

(71) Applicant: Jason M. Evans, Flint, MI (US)

(72) Inventor: Jason M. Evans, Flint, MI (US)

(*) Notice: Subject to any disclaimer, the term of this patent is extended or adjusted under 35 U.S.C. 154(b) by 50 days.

(21) Appl. No.: 16/227,982

(22) Filed: Dec. 20, 2018

(51) Int. Cl.
*A61B 17/22* (2006.01)
*A61B 18/26* (2006.01)
*A61M 3/02* (2006.01)
*A61B 18/00* (2006.01)

(52) U.S. Cl.
CPC .............. *A61B 17/22* (2013.01); *A61B 18/26* (2013.01); *A61M 3/0279* (2013.01); *A61B 2017/22079* (2013.01); *A61B 2017/22082* (2013.01); *A61B 2018/00511* (2013.01); *A61M 2206/20* (2013.01); *A61M 2210/1082* (2013.01)

(58) Field of Classification Search
CPC .................... A61B 17/22; A61B 18/26; A61B 2018/00511; A61B 2017/22082; A61B 2017/22079; A61M 3/0279; A61M 2210/1082; A61M 2206/20
See application file for complete search history.

(56) References Cited

U.S. PATENT DOCUMENTS

| | | | | |
|---|---|---|---|---|
| 2004/0267213 | A1* | 12/2004 | Knapp | A61B 1/307 604/284 |
| 2014/0364868 | A1* | 12/2014 | Dhindsa | A61B 18/245 606/127 |
| 2015/0273129 | A1* | 10/2015 | Freeman | A61M 1/3679 210/698 |
| 2016/0256628 | A1* | 9/2016 | Lee | A61M 5/16877 |
| 2017/0215964 | A1* | 8/2017 | Harrah | A61B 18/245 |

\* cited by examiner

*Primary Examiner* — Lauren P Farrar

(57) ABSTRACT

A method of removing a kidney stone from the kidney and ureter of a human includes the steps of introducing a laminar flowing fluid via a ureteroscope into the ureter or kidney and proximal the kidney stone and flowing inward toward the kidney and then switching the laminar flow to a turbulent flow which causes a reverse flow that moves the kidney stone in a direction away from the kidney and down the ureter toward the bladder where the stone may be removed using a wire basket. In one step the kidney stone may first be fragmented into smaller kidney stones or fragments prior to switching to the turbulent flow.

13 Claims, 3 Drawing Sheets

KIDNEY STONE TURBULENT FLOW IRRIGATOR AND SYSTEM

CROSS-REFERENCE TO RELATED APPLICATIONS

This application claims priority to and benefit of U.S. Provisional Patent Application Ser. No. 62/608,199, filed Dec. 20, 2017 entitled KIDNEY STONE TURBULENT FLOW IRRIGATOR AND SYSTEM in the name of Jason Evans, the entire contents of which are incorporated herein for all purposes.

FIELD

The present disclosure relates generally to a method and system for removing kidney stones and fragments.

BACKGROUND

The statements in this section merely provide background information related to the present disclosure and may not constitute prior art.

Various organs and passages in the body are subject to the development of stones, calculi and the like. For example, kidney stones are a common problem for humans. They can be quite painful and are the most frequent cause of kidney inflammation. Calculi and concretions in other parts of the biliary system also occur. Similarly, stones, calculi, concretions and the like can develop throughout the renal or urinary system, not only in the ureters and distal to them, but also in the renal tubules and in the major and minor renal calyxes.

Minimally invasive surgical procedures have been developed for the removal of stones, calculi, concretions and the like from the biliary, vascular, and urinary systems, as well as for the removal or retrieval of foreign bodies from a variety of locations in the body. Such procedures avoid the performance of open surgical procedures such as, for example, an anatrophic nephrolithotomy. Minimally invasive procedures can instead employ urethra cystoscopy access, in which stones, calculi, concretions, foreign bodies and the like are removed through an endoscopy device including an access sheath. The urethra cystoscopy route of access is suitable, depending upon the specific organ and the particular location in the organ for removing the stones, calculi, concretions, foreign bodies or the like.

Urethra extraction may be based upon the use of catheters, cystoscopes, endoscopes, and similar devices to locate, engage, break up, destroy, and/or remove the unwanted object or body. The devices used in removing the kidney stone typically comprise a hollow, flexible sheath and a plurality of wires positioned in and extendable from the sheath. The wires are joined or arranged to form a capturing device, such as basket or forceps for engaging, capturing and removing the object when the wires are extended from the sheath and then drawn back in the sheath with the object captured by the wires and the end of the sheath. The capturing device or means (for example, a stone retrieval wire basket) may be collapsed by moving the wires back into the sheath. A helical basket permits entry of the stone or the like from the sides of the basket, while an open ended (sometimes generally referred to as an "egg whip") basket allows a more direct or head-on approach to the object to be captured, blasted/broken up and removed. Other retriever and grasper type devices may include forceps and a loop or snare wire device for encircling the object. Such retrieval devices may be used in conjunction with other devices and procedures, such nephoscopy, to aid the physician in observing and performing the removal procedures.

Despite their successful use for some time, such retrieval devices include certain known drawbacks and limitations. One known device that is used to retrieve objects, such as kidney stones, is a 3-pronged grasper. The prongs of the grasper, useful in grasping stones, may cause damage to kidney or contiguous tissue, leading to internal bleeding, and potentially significantly extending the time for the procedure. The very flexible, movable nature of these wire sprung graspers adds to the problem, in that their flexibility and mobility may also make them more challenging to control.

While the prior art devices and constructions may be adequate for the basic purpose and function for which they have been specifically designed, they are uniformly deficient with respect to their failure to provide a simple, efficient, and practically useful portable stone retrieval device that is easier and more efficient to use and may eliminate at least some of the problems of the prior art devices as well as eliminate the need for the prior art devices. Accordingly, there long exists a continuing need for a new and improved method and device for removing a kidney stone.

SUMMARY

The present disclosure provides for a method of removing objects from a patient. The method may include the steps of introducing a pressurized fluid into a cavity in the patient and located proximate an object to be removed; adjusting the flow dynamics of the fluid using a filter to generate a desired turbulent inflow; and forming a vacuum effect through the turbulent flow operable to cause the fragments to continue through the body system to a desired location (i.e., bladder) for easier and safer removal.

The present disclosure further provides for a turbulent flow irrigation device and process. The device may include a tube operable for delivering fluid to a desired location within a body, a filter for restricting fluid flow passage through the tube; and a switch operable for activating the filter to position within a flow path of the tube. The filter is operable to generate turbulent fluid flow sufficient to form a pressure differential effect within the body. Further areas of applicability will become apparent from the description provided herein. The description and specific examples are intended for purposes of illustration only and are not intended to limit the scope of the present disclosure.

BRIEF DESCRIPTION OF THE DRAWINGS

There will now be described in detail various forms of the disclosure, given by way of examples with reference being made to the accompanying drawings in which.

Figure 1:
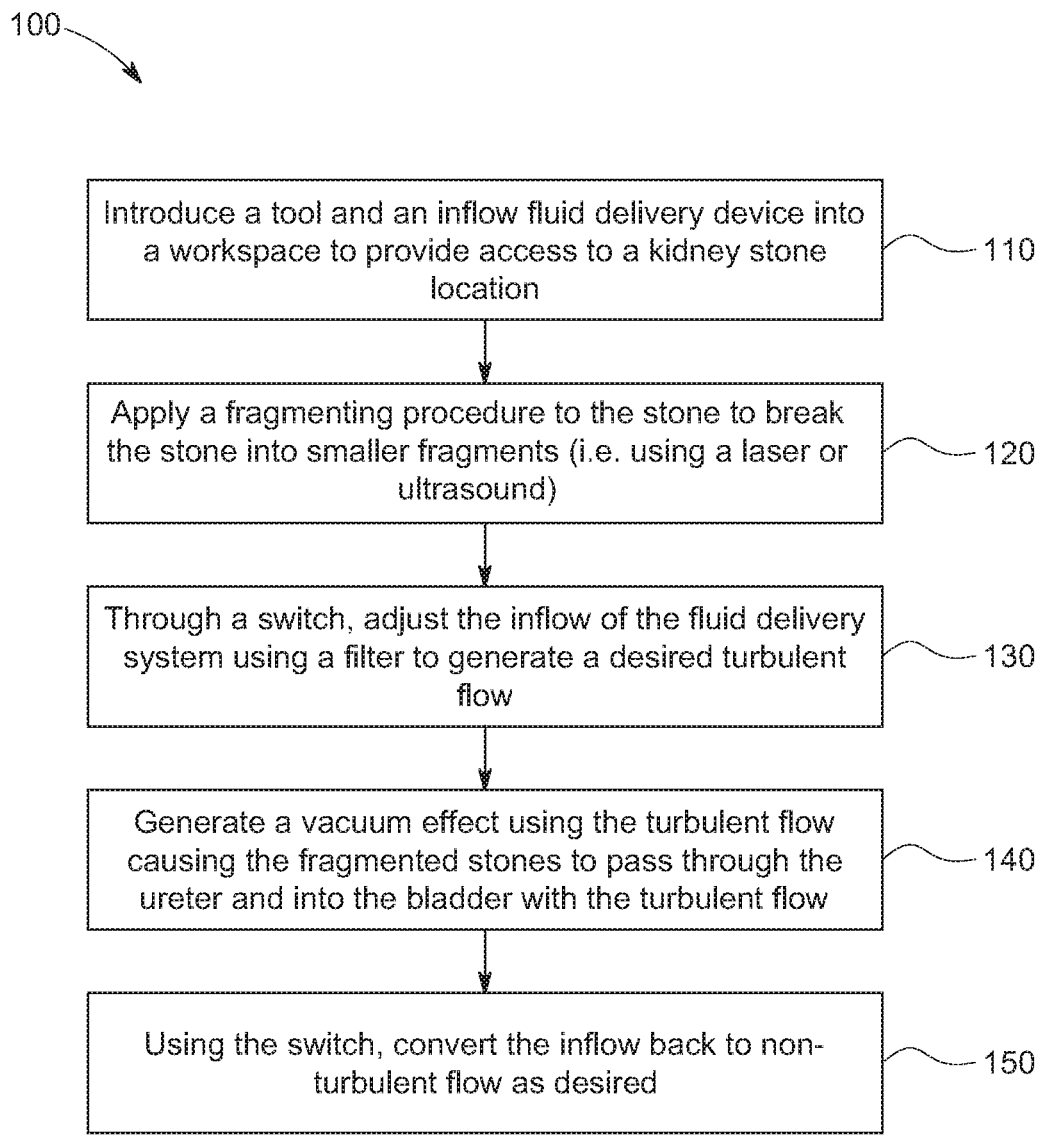
FIG. 1 is a flow diagram of an exemplary method of removing kidney stones according to the present disclosure.

The drawings described herein are for illustration purposes only and are not intended in any way to limit the scope of the present disclosure.

DETAILED DESCRIPTION

The following description is exemplary in nature and is not intended to limit the present disclosure and claims.

Throughout the drawings, corresponding reference numerals indicate like or corresponding parts and features.

FIG. 1 discloses a flow diagram of a method of removing an object (e.g., a kidney stone) from a patient using a cystoscope or ureteroscope inserted via the patient's urethra. The method 100 may include step of using an inflow fluid delivery device as introduced near the stone during step 110. The fluid delivery device may be operable as an irrigation system to flush out the object (and/or particles of the object one) into the ureter and continue to the bladder where the undesired objects may be more easily and safely removed from the patient. The method 100 may alternately include an ablation step 120 where an ablation device may be introduced and used to fragment the object (i.e., the kidney stone) into smaller particles to be removed. This step may be particularly appropriate when a relatively large-size object to be removed is in an undesired location within the patient, such as in the kidney. The ablation step 120 may also be used when the object is too large to be removed via the ureter.

One type of known ablation device is a laser including a fiber optic wire that may be introduced by a surgeon to focus laser energy on the object to generate fragments of the kidney stone. This ablation step shown in box 120 may also be referred to as a fragmenting method step. Additionally, the method 100 may include sub-fragmenting method steps and procedures until the objects are broken up into sufficiently small pieces to travel through the patient's ureter. Further, other types of devices for breaking up or eliminating objects or stones, such as ultrasound, are contemplated within the scope of the present disclosure.

The method of removing an object 100 may further include the method step 130 of operating a switch for activating a filter in the fluid delivery device. The filter may be operable to generate a change in the fluid flow dynamics of the inflow fluid, for example, generating a turbulent flow. Turbulent flow is generally understood to be a type of fluid (gas or liquid) flow in which the fluid undergoes fluctuations, or mixing, in contrast to laminar flow, in which the fluid moves in predictable paths or layers. Generally, in turbulent flow the velocity and pressure of the fluid at a point are undergoing changes in both magnitude and direction. In this context, the term "turbulent flow" is meant to generate a flow that is operable to create a pressure differential within the particular body part or workspace as shown in method step 140. The vacuum effect is sufficient to draw the fragmented stone pieces out of the kidney and into the ureter where they can continue to pass into the bladder of from the ureter directly into the bladder. A switch on the fluid flow device may be used to covert the inflow fluid back to a non-turbulent flow as desired as shown in box 150. Accordingly, the surgeon can use this switch as desired to cause migration of the stone to a more suitable location to have better access for fragmenting or to prevent the stone from getting stuck in an undesired location.

Figure 2:
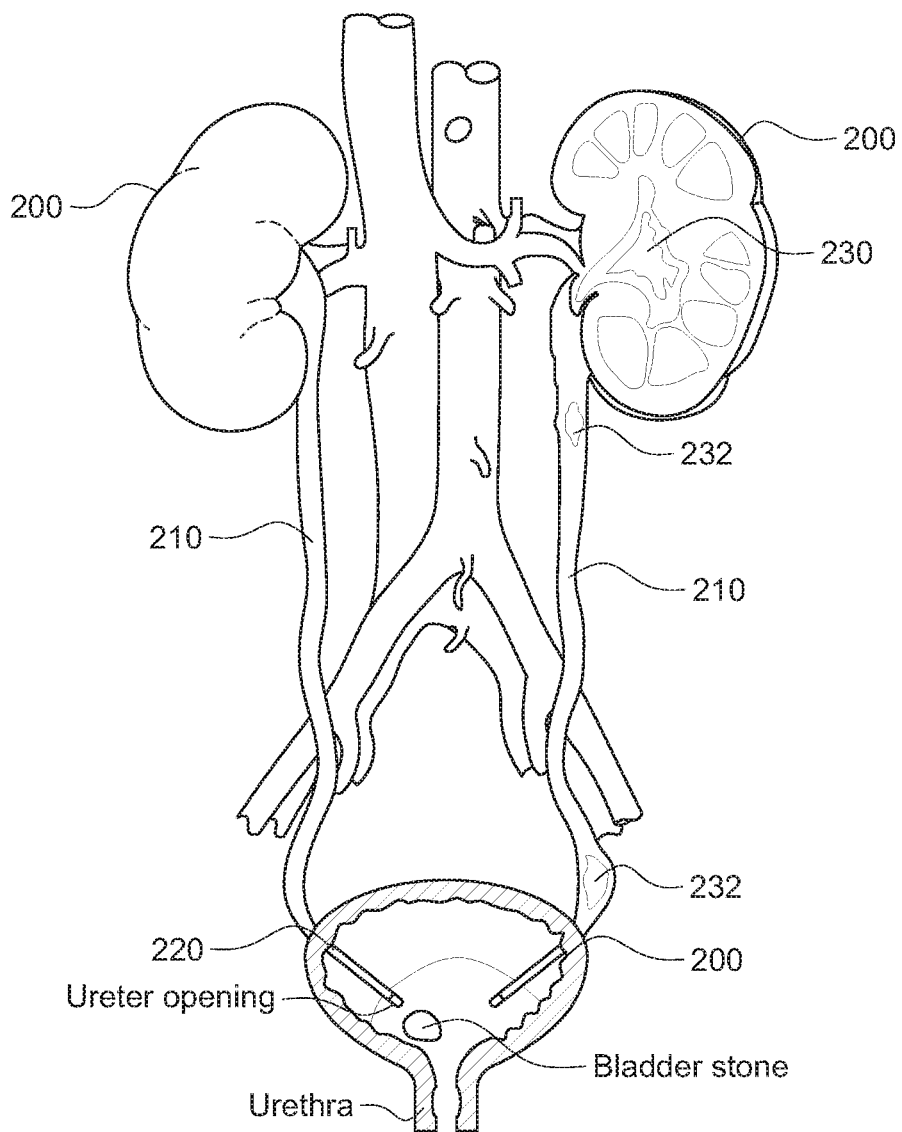
FIG. 2 is a diagram illustrating fragmenting a kidney stone and removal of fragments of a kidney stone associated with the present disclosure.
Figure 3:
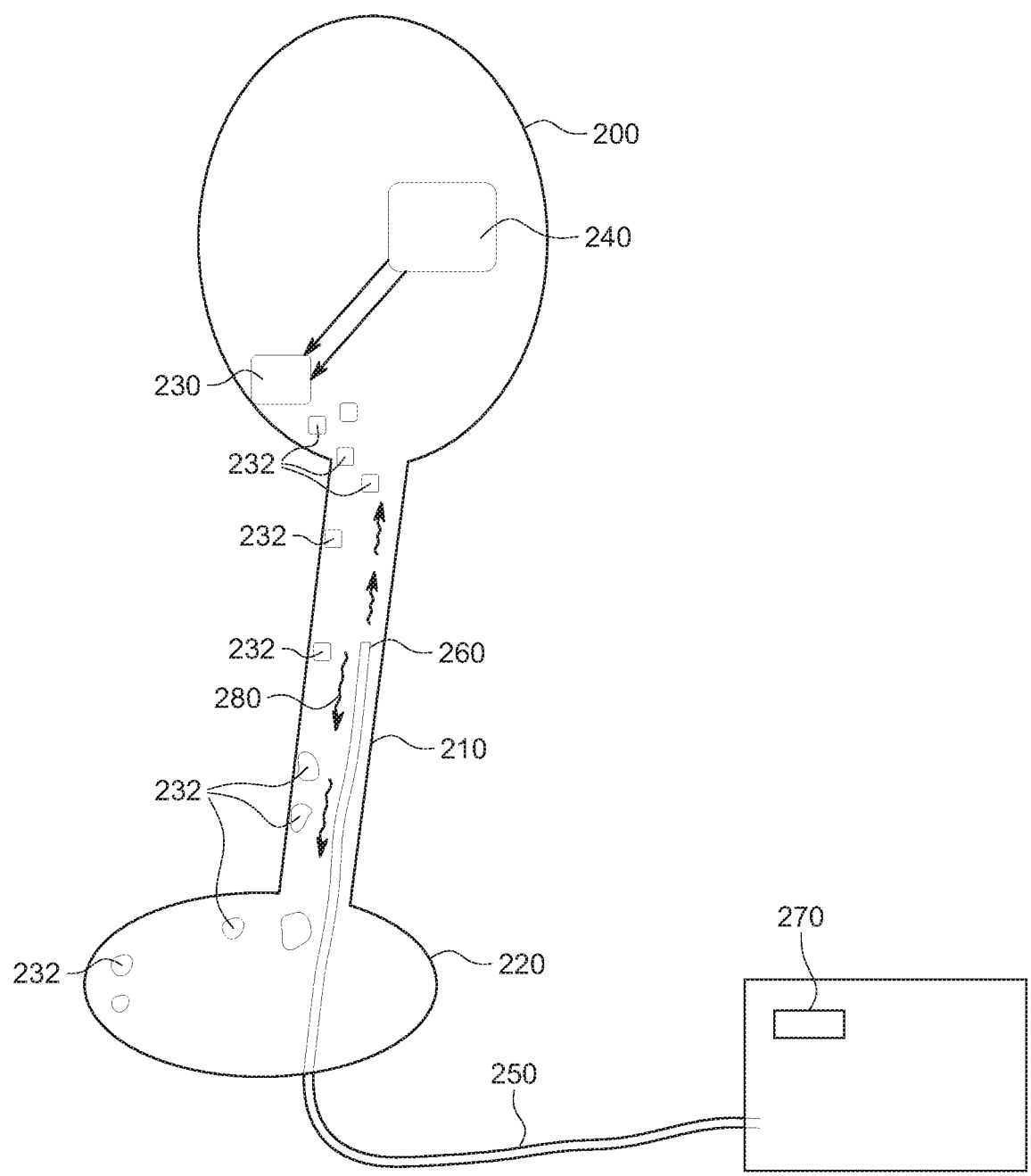
FIG. 3 is a graphical diagram illustrating the method as used in the body and a device for implementing the method.

Referring now to FIGS. 2 and 3, there is shown a partial diagram of a kidney, ureter and bladder of a human. Kidney 200 is connected to ureter 210 which communicates with bladder 220. Also shown is a kidney stone 230 in the kidney 200 which stone 230 may be exposed to the fragmenting process 120, such as a laser inserted through a ureteroscope, to generate smaller stone fragments 232. The Ureteroscope may include a sheath and an internal passageway to allow for introducing additional instruments. In this example, an irrigating system may be introduced to the area of the kidney 200 and/or the ureter 210 where the stone fragments 232 are located. The irrigation system includes a fluid delivery apparatus for generating inflow of fluid to flush out the area of remaining fragments. Included in scope 250 is a filter or other mechanical type device 260 which may be activated by a switch 270 by a surgeon or user. Activating the filter 260 generates an increased and/or varied flow rate of the fluid. Accordingly, a turbulent flow 280 is generated which creates a vacuum effect which may be moved or directed about the stone fragments 232. This results in the fluid flow pulling fragments 232 away from the kidney and into the ureter 210 and ultimately through the ureter 210 and into the bladder 200. The switch 270 on the irrigation system or scope 250 can then be converted back to normal or non-turbulent flow when desired.

As can be appreciated from the above, the method and system of the present disclosure provides for moving a stone within the body without the need or use of inserting a basket or retrieval device. Flow fluid adjustment (i.e., selectively using turbulent flow) allows the surgeon to move the stone distal the kidney 200 and ureter 210 for further treatment instead of it migrating into an undesired location within the kidney 200 which may require a different scope and fiber and to perform additional procedures adding cost and time.

It should also be appreciated form the above that this same method allows for manipulation and movement of the stone 230 within the kidney 200. For example, if a surgeon were to have a lower pole stone that they desired in a more optimal location for treatment such as a mid or upper calyx, the turbulent flow 280 could again be activated to move the stone 230 into a more desired location for further treatment. The method and system allow one to move a stone while minimizing or eliminating having to introduce a basket or grasping device that may become stuck in the kidney while moving the stone.

It is contemplated that in the lower portions of the ureter 210 proximal the bladder 220 a natural obstruction of the ureter 210 diving into the pelvis provides partial resistance that allows the fragments 232 to more easily migrate down the ureter 210 with the turbulent flow irrigator of the present disclosure.

Advantages of the turbulent flow irrigator system of the present disclosure include but are not limited to:
1) Reduce or eliminate a need to add additional equipment once the stone is fragmented to remove pieces. The use of baskets could be reduced and/or eliminated in such cases saving the surgeon and facility time and money;
2) Reduce or eliminate danger of engaging a stone and having the basket or grasping device become stuck in the ureter or kidney; and
3) Provide a way to actively pull a stone and/or fragments toward the bladder during laser fragmentation if the pieces start to migrate during treatment with normal irrigation.

The foregoing description of various forms of the present disclosure has been presented for purposes of illustration and description. It is not intended to be exhaustive or to limit the present disclosure to the precise forms disclosed. Numerous modifications or variations are possible considering the above teachings. The forms discussed were chosen and described to provide the best illustration of the principles of the present disclosure and its practical application to thereby enable one of ordinary skill in the art to utilize the present disclosure in various forms and with various modifications as are suited to the particular use contemplated. All such modifications and variations are within the scope of the present disclosure as determined by the appended claims when interpreted in accordance with the breadth to which they are fairly, legally, and equitably entitled.

What is claimed is:

1. A method of removing fragments found in a patient, the method comprising:
   introducing a pressurized fluid into a cavity in the patient and located proximate the fragments to be removed;
   adjusting the flow dynamics using a filter to generate a desired turbulent inflow including a lower pressure area and a higher pressure area forming a variable and directable vacuum effect;
   directing the turbulent inflow to align the vacuum effect proximal the fragments to cause the fragments to move to a desired location more distal from the kidney to be removed from the patient.

2. The method of claim 1, wherein the cavity is located within a kidney of the patient and the fragments are generated from a fragmenting process applied to a kidney stone.

3. The method of claim 2, wherein the vacuum effect is sufficient to cause the fragments to pass from a kidney through a ureter and further into a bladder.

4. The method of claim 1, wherein the filter is coupled to a switch to be activated and deactivated to modify the flow dynamics from turbulent to non-turbulent flow.

5. The method of claim 1, further comprising a fragmenting step applied to an object intended to be removed from the patient body, wherein the fragmenting step includes introducing an object destruction device.

6. The method of claim 5, further comprising the step of using a ureteroscope for supplying the pressurized fluid within the patient and wherein the pressurized fluid is introduced through the ureteroscope once the fragmenting step is complete.

7. The method of claim 1, wherein the fragments are removed from the patient without the use of a retrieval device.

8. A turbulent flow irrigation device comprising:
   a tube operable for delivering fluid to a desired location within a body;
   a filter for restricting fluid flow passage through the tube;
   a switch operable for activating the filter to position within a flow path of the tube;
   wherein the filter is selectively operable to switch between a laminar fluid flow and a turbulent fluid flow sufficient to form a vacuum effect within the body wherein the vacuum effect may be located proximal a kidney stone to move the kidney stone more distal from the kidney.

9. A method of removing a kidney stone from a ureter and a kidney of a patient, the method comprising the steps of:
   introducing a laminar flowing fluid into the ureter and kidney in the patient including the fragment to be removed;
   changing the laminar flowing fluid to a turbulent flowing fluid to form a vacuum effect proximal the fragment to cause the stone to move through the cavity to a desired location more distal the kidney.

10. The method of claim 9, further comprising the step of fragmenting the kidney stone into smaller pieces and then selectively applying the turbulent flowing fluid to move the fragments toward the bladder.

11. The method of claim 9, further comprising the step of selectively actuating a switch change between laminar flow and turbulent flow.

12. The method of claim 11, wherein the fragmenting step is completed prior to switching from laminar flow to turbulent flow.

13. The method of claim 9, further comprising the step of inserting a wire basket into the bladder and capturing the stone once the stone is moved to the bladder using the turbulent flow thereby eliminating the need to insert the basket into the ureter and the kidney.

* * * * *